United States Patent
Abdulwahed et al.

(10) Patent No.: US 6,486,091 B1
(45) Date of Patent: *Nov. 26, 2002

(54) PROCESS FOR MAKING HIGHLY ACTIVE AND SELECTIVE CATALYSTS FOR THE PRODUCTION OF UNSATURATED NITRILES

(75) Inventors: Mazhar Abdulwahed, Damascus (SY); Khalid El-Yahyaoui, Meknes (MA)

(73) Assignee: Saudi Basic Industries Corporation, Riyadh (SA)

( * ) Notice: Subject to any disclaimer, the term of this patent is extended or adjusted under 35 U.S.C. 154(b) by 52 days.

(21) Appl. No.: 09/675,599

(22) Filed: Sep. 29, 2000

Related U.S. Application Data

(60) Provisional application No. 60/189,215, filed on Mar. 14, 2000.

(51) Int. Cl.$^7$ .................. B01J 23/20; B01J 23/22; B01J 23/28; B01J 23/31; B01J 23/18
(52) U.S. Cl. .................. 502/312; 502/311; 502/321; 502/353
(58) Field of Search .................. 502/311, 312, 502/313, 317, 306, 321, 353

(56) References Cited

U.S. PATENT DOCUMENTS

| | | | |
|---|---|---|---|
| 3,057,915 A | 10/1962 | Riemenschneider et al. | |
| 3,131,223 A | 4/1964 | Smidt et al. | |
| 3,240,805 A | 3/1966 | Naglieri | |
| 3,301,905 A | 1/1967 | Riemenschneider et al. | |
| 3,872,148 A | 3/1975 | Umemura et al. | 260/465.3 |
| 4,018,713 A * | 4/1977 | Bushick et al. | 502/344 |
| 4,040,978 A | 8/1977 | Li | 252/437 |
| 4,062,885 A | 12/1977 | Mekhtiev et al. | 260/465 |
| 4,148,757 A | 4/1979 | Brazdil et al. | 252/432 |
| 4,190,556 A | 2/1980 | Grasselli et al. | 252/432 |
| 4,250,346 A | 2/1981 | Young et al. | 585/658 |
| 4,292,203 A | 9/1981 | Milberger et al. | 252/438 |
| 4,339,355 A | 7/1982 | Decker et al. | 252/464 |
| 4,405,498 A | 9/1983 | Ebner | 252/432 |
| 4,413,155 A * | 11/1983 | Suresh et al. | 558/321 |
| 4,423,281 A | 12/1983 | Yamamoto et al. | 585/626 |
| 4,487,850 A | 12/1984 | Li | 502/249 |
| 4,524,236 A | 6/1985 | McCain | 585/658 |
| 4,547,484 A | 10/1985 | Li | 502/249 |
| 4,568,790 A | 2/1986 | McCain | 585/658 |
| 4,596,787 A | 6/1986 | Manyik et al. | 502/312 |
| 4,600,541 A | 7/1986 | Aoki et al. | 558/321 |
| 4,746,641 A * | 5/1988 | Guttmann et al. | 502/202 |
| 4,788,173 A | 11/1988 | Glaeser et al. | 502/204 |
| 4,899,003 A | 2/1990 | Manyik et al. | 585/313 |
| 5,049,692 A | 9/1991 | Hatano et al. | 558/319 |
| 5,132,269 A | 7/1992 | Sasaki et al. | 502/205 |
| 5,162,578 A | 11/1992 | McCain, Jr. et al. | 562/512.2 |
| 5,198,580 A | 3/1993 | Bartek et al. | 562/542 |
| 5,300,682 A | 4/1994 | Blum et al. | 562/512.2 |
| 5,364,825 A | 11/1994 | Neumann et al. | 502/311 |
| 5,472,925 A | 12/1995 | Ushikubo et al. | 502/312 |
| 5,688,739 A | 11/1997 | Drenski et al. | 502/308 |
| 5,808,143 A | 9/1998 | Karrer et al. | 562/407 |
| 5,821,192 A | 10/1998 | Seeley et al. | 502/353 |
| 5,866,502 A | 2/1999 | Cirjak et al. | 502/353 |
| 5,907,052 A | 5/1999 | Hamada et al. | 558/320 |
| 6,017,846 A * | 1/2000 | Abdulwahed et al. | 502/312 |
| 6,037,304 A * | 3/2000 | Abdulwahed et al. | 502/312 |
| 6,043,185 A * | 3/2000 | Cirjak et al. | 502/311 |
| 6,063,728 A * | 5/2000 | Hinago et al. | 502/300 |
| 6,124,233 A * | 9/2000 | Abdulwahed et al. | 502/312 |
| 6,143,690 A * | 11/2000 | Komada et al. | 502/211 |

FOREIGN PATENT DOCUMENTS

| | | |
|---|---|---|
| EP | 0 032 012 | 7/1981 |
| EP | 0 475 351 | 3/1992 |
| EP | 0 573 713 | 12/1993 |
| EP | 0 603 836 | 6/1994 |
| EP | 0 945 432 | 9/1999 |

* cited by examiner

Primary Examiner—Stanley S. Silverman
Assistant Examiner—Christina Ildebrando
(74) Attorney, Agent, or Firm—Kramer Levin Naftalis & Frankel LLP

(57) ABSTRACT

An improved catalyst for the production of unsaturated nitrites from their corresponding olefins, the catalyst having the atomic ratios described by the empirical formula $Bi_a Mo_b V_c Sb_d Nb_e A_f B_g O_x$ and methods of making and using the same.

40 Claims, No Drawings

PROCESS FOR MAKING HIGHLY ACTIVE AND SELECTIVE CATALYSTS FOR THE PRODUCTION OF UNSATURATED NITRILES

This application claims the benefit of provisional application Ser. No. 60/189,215, filed Mar. 14, 2000.

RELATED APPLICATIONS

This application is related to U.S. patent application Ser. No. 09/228,885, filed Jan. 11, 1999, now U.S. Pat. No. 6,037,304, issued Mar. 14, 2000 and U.S. patent application Ser. No. 09/431,744, filed Nov. 1, 1999, allowed, each of which are incorporated herein by reference.

BACKGROUND OF THE INVENTION

1. Field of the Invention

The present invention relates to methods of making improved ammoxidation catalysts for the production of unsaturated nitriles from their corresponding olefins.

2. Description of Related Art

Several publications are referenced in this application. The references describe the state of the art to which this invention pertains and are hereby incorporated by reference.

It is known in the art that the bismuth-molybdenum system plays a role in electron donor/acceptor mechanisms for selective oxidation and ammoxidation. Therefore different mechanisms have been proposed based on this property [Delmon et al. (New Development in Selective Oxidation by Heterogeneous Catalysis, Vol. 72, 1992, p. 399–413) and Encyclopedia of Chemical Technology (Kirk-Othmer, Vol. 1, 4th edition, page 358)]. In these mechanisms, molybdenum was shown to be responsible for oxygen and nitrogen uptake and insertion into the substrate, while bismuth plays the role of H-abstraction of the methyl group in the $\beta$ position. Therefore, bismuth and molybdenum should be present on the catalyst surface and adjacent in order to form the suitable active phase for this reaction. It should be noted that the deficiency of bismuth on the catalyst surface leads to the total oxidation reaction of the substrate.

It is also well known that antimony plays the role of a donor and thus could improve the selectivity of the catalyst. Antimony can also play an additional role of isolating the vanadium active centers which are highly active towards the oxidation reaction. This leads to minimizing the total oxidation reaction and directs the reaction towards the desired product.

Many catalysts have been disclosed for the foregoing reactions. One such catalyst is described in U.S. Pat. No. 4,062,885, where BiMoSbV systems were used as active elements. The catalyst was used for the preparation of phthalonitrile by the ammoxidation of ortho-xylene. The use of such catalysts for oxidation or ammoxidation reactions involving unsaturated aliphatic hydrocarbons is not mentioned.

U.S. Pat. No. 4,040,978 relates to a catalyst for ammoxidation reactions containing bismuth molybdate mixed with other elements.

U.S. Pat. No. 4,405,498 relates to a catalyst for oxidation and ammoxidation reactions containing BiMoVSb with additional elements selected from groups IA, IIA, IVA, VA, VIA, IB, IVB and VIIB of the periodic Table of the Elements. Elements from group VB of the periodic table are not disclosed in this patent.

U.S. Pat. No. 4,600,541 relates to a catalyst comprising FeBiMo and promoters such as Pd, Pt, Os and Ir.

More recently, European Patent Publication No. 0 475 351 A1 relates to a catalyst containing KFeSbMo which could be promoted by Nb and W. The best yield was achieved with a catalyst of the formula $Fe_{10}Sb_{10}Mo_9Bi_2K_{0.6}Ni_{5.5}W_{0.3}B_{0.75}P_{0.75} (SiO_2)_{70}$.

European Patent Publication No. 0 573 713 B1 relates to a catalyst comprising MoBiFeCoNiCr promoted with at least three other promoters selected from alkali metals, alkaline earth metals, rare earth metals, Nb, Tl and As, with Fe, Co, Ni and Cr as essential catalyst components.

U.S. Pat. No. 5,688,739 relates to a multi-component catalyst. The base of this catalyst is bismuth molybdenum. Germanium was added as an essential element. The use of niobium was not disclosed in this patent.

None of the prior art references discloses or suggests catalysts which provide high performance for the selective production of unsaturated nitrites from their corresponding olefins. Accordingly, it would be desirable to produce an improved catalyst for use in the selective production of unsaturated nitrites from their corresponding olefins.

OBJECTS OF THE INVENTION

It is an object of the invention to overcome the above-identified deficiencies.

It is another object of the invention to provide a useful, improved catalyst for the production of nitrites from their corresponding olefins, particularly for the production of acrylonitrile from propylene.

It is a further object of the invention to provide a process for making an improved catalyst for the production of acrylonitrile at high yields by vapor phase catalytic ammoxidation of propylene in a fluidized or fixed bed reactor.

The foregoing and other objects and advantages of the invention will be set forth in or apparent from the following description.

SUMMARY OF THE INVENTION

The present invention relates to an improved catalyst for the production of unsaturated nitrites from their corresponding olefins and methods of making and using the same. More specifically, the invention relates to improved methods of making such catalysts and the resultant improved catalysts.

Preferably, the catalyst has the following empirical formula set forth below:

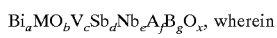, wherein

A=one or more elements selected from groups VB (e.g. V, Nb, Ta), VIB (e.g. Cr, Mo, W), VIIB (e.g. Mn, Tc, Re) or VIII (e.g. Fe, Co, Ni) of the periodic table;

B=at least one alkali promoter selected from groups IA (e.g., Li, Na, K) or IIA (e.g., Mg, Ca) of the periodic table;

a=0.01 to 12;
b=0.01 to 12;
c=0.01 to 2;
d=0.01 to 10;
e=0.01 to 1;
f=0 to 2, preferably from 0.01 to 1;
g=0 to 1, preferably from 0.001 to 0.5; and
x=the number of oxygen atoms required to satisfy the valency requirements of the elements present.

The numerical values of a, b, c, d, e, f, g, and x represent the relative gram-atom ratios of the elements, respectively, in the catalyst, where x is a number required to satisfy the valence requirements of the other elements. The elements are present in combination with oxygen, preferably in the form of various oxides.

The invention also relates to an improved selective low temperature catalytic process for the production of nitrites from their corresponding olefins, particularly for the production of acrylonitrile from propylene.

Other objects as well as aspects, features and advantages of the present invention will become apparent from a study of the present specification, including the claims and specific examples.

DESCRIPTION OF THE PREFERRED EMBODIMENTS

One aspect of the invention relates to methods for preparing catalysts for the production of unsaturated nitrites.

One embodiment of the invention relates to a method for preparing a catalyst for olefin ammoxidation, said catalyst containing bismuth, molybdenum, vanadium, antimony, and niobium, comprising the steps of:

(a) preparing a vanadium antimonate phase by heating a slurry of vanadium oxide and antimony oxide thereby forming a vanadium-antimony paste and subsequently drying the paste and calcining to form said vanadium antimonate phase;

(b) preparing a niobium-molybdenum solution;

(c) preparing bismuth, niobium, and molybdenum mixed oxide hydrates at room temperature and without heat treating said mixed oxide hydrates;

(d) combining said vanadium antimonate phase, said mixed oxide hydrates and a support thereby forming a catalyst precursor mixture;

(e) stirring the catalyst precursor mixture for a period of time sufficient to form a catalyst precursor paste; and (f) drying said catalyst precursor paste to form a dried catalyst precursor material and calcining said dried catalyst precursor material to form said catalyst.

Preferably, the catalyst has the following empirical formula:

$Bi_aMo_bV_cSb_dNb_eA_fB_gO_x$, wherein:

A=one or more elements selected from the group consisting of groups VB, VIB, VIIB, and VIII of the periodic table;
B=at least one alkali promoter selected from the group consisting of groups IA and IIA of the periodic table;
a=0.01 to 12;
b=0.01 to 12;
c=0.01 to 2;
d=0.01 to 10;
e=0.01 to 1;
f=0 to 2, preferably from 0.01 to 1;
g=0 to 1, preferably from 0.001 to 0.5; and
x=the number of oxygen atoms required to satisfy the valency requirements of the elements present.

Preferably, the vanadium oxide is $V_2O_5$ and/or the antimony oxide is $Sb_2O_3$.

Preferably, the calcining in step (a) is at a temperature ranging from 600 to 950° C., more preferably 700 to 850° C., even more preferably from 740 to 780° C. and most preferred about 750° C.

Preferably the calcining in step (a) is in the presence of air and/or oxygen.

Preferably, the niobium-molybdenum solution is prepared at a pH of 3.0 to 10, more preferably a pH of 3.5 to 9, even more preferably a pH of 3.5 to 5.

According to one preferred embodiment, step (c) comprises adding bismuth to said niobium-molybdenum solution and precipitating said mixed oxide hydrates at room temperature and without heat treating of said mixed oxide hydrates.

Preferably, step (c) comprises rash co-precipitation of bismuth, niobium, and molybdenum mixed oxide hydrates. More preferably, step (c) comprises adding a solution containing bismuth to said niobium-molybdenum solution.

According to one preferred embodiment, the support comprises pre-acidified silica. Preferably, step (d) comprising incorporating said vanadium antimonate phase and said mixed oxide hydrates in pre-acidified silica colloidal.

According to another preferred embodiment, the method further comprises boiling said catalyst precursor mixture to form said catalyst precursor paste.

Preferably, the stirring in step (e) is vigorous stirring, as opposed to gentle or mild stirring.

According to one preferred embodiment, the catalyst precursor paste is dried at a temperature ranging from 80° C. to 200° C., preferably from 100° C. to 150° C., more preferably from 110° C. to 130° C. and most preferred about 120° C.

According to another preferred embodiment, the calcining of said dried catalyst precursor material is at a temperature ranging from 450 to 650° C., more preferably from 500 to 600° C., even more preferably about 550° C.

Preferably, the calcining of said dried catalyst precursor material is under an airflow or in the presence of air.

The catalysts of the invention can be used with or without a support. Preferably, the catalyst is a support ed catalyst. Suitable supports for the catalysts include alumina, silica, titania, zirconia, zeolites, silicon carbide, carbide, molecular sieves and other micro/nonporous materials, and mixtures thereof. When used on a support, the supported catalyst usually comprises from about 10 to 50% by weight of the catalyst composition, with the remainder being the support material.

Preferably, the support is selected from silica, alumina, zirconia, titania, alundum, silicon carbide, alumina-silica, inorganic phosphates, silicates, aluminates, borates and carbonates, pumice, montmorillonite, or mixtures thereof. More preferably, the support is silica. Preferably, the resultant catalyst comprises 40–70% by weight support.

According to another embodiment, the catalyst contains niobium derived from niobium pentoxide or niobium derived from a niobium source soluble in water. Preferably, the niobium-molybdenum solution is prepared using niobium derived from niobium pentoxide or using niobium derived from a niobium source soluble in water.

Preferably, step (a) comprises drying said paste at a temperature ranging from 80° C. to 200° C., more preferably from 100° C. to 150° C., even more preferably from 110° C. to 130° C. and most preferred about 120° C.

Another embodiment of the invention relates to a method for preparing a catalyst for olefin ammoxidation, said catalyst containing bismuth, molybdenum, vanadium, antimony, and niobium, comprising the steps of;

(a) preparing a niobium-molybdenum solution at a pH of 3.5 to 10;

(b) adding bismuth to said niobium-molybdenum solution and precipitating bismuth, niobium, and molybdenum mixed oxide hydrates at room temperature and without heat post-treatment of said mixed oxide hydrates;

(c) combining a vanadium antimonate phase and said mixed oxide hydrates of bismuth, niobium, and molybdenum with pre-acidified silica colloidal thereby forming a catalyst precursor mixture;

(d) stirring the catalyst precursor mixture for a period of time sufficient to form a paste; and (e) drying said paste to form a dried material and calcining said dried material to form said catalyst.

Yet another embodiment of the invention relates to a method for preparing a catalyst for olefin ammoxidation, said catalyst containing bismuth, molybdenum, vanadium, antimony, and niobium, comprising the steps of:

(a) preparing a vanadium antimonate phase;

(b) preparing a niobium-molybdenum solution at a pH of 3.5 to 10 ;

(c) adding bismuth to said niobium-molybdenum solution and precipitating bismuth, niobium, and molybdenum mixed oxide hydrates without heat post-treatment of said mixed oxide hydrates;

(d) combining said vanadium antimonate phase and said mixed oxide hydrates of bismuth, niobium, and molybdenum with pre-acidified silica colloidal thereby forming a catalyst precursor mixture;

(e) stirring the catalyst precursor mixture for a period of time sufficient to form a paste; and (f) drying said paste to form a dried material and calcining said dried material to form said catalyst.

One particularly preferred embodiment of the invention relates to a method of making an improved ammoxidation catalytic system for the production of unsaturated nitriles from their corresponding olefins, in particular, for the production of acrylonitrile from propylene. More specifically, the present invention is directed to a method of making an improved ammoxidation catalyst containing niobium as an essential element for enhancing activity and selectivity of the catalyst system.

Another preferred embodiment of the invention relates to methods of making the catalysts described in copending U.S. application Ser. No. 09/228,885, filed Jan. 11, 1999, now U.S. Pat. No. 6,037,304, issued Mar. 14, 2000.

The Examples set forth below demonstrate the advantages achieved using the invention by showing the surprising effect of certain factors in preparing the catalyst.

Another aspect of the invention relates to methods of using the catalyst system of the invention. More specifically, the invention relates to an improved method of producing unsaturated nitriles from their corresponding olefms.

One preferred embodiment of the invention relates to an improved process for the catalytic preparation of acrylonitrile or metha acrylonitrile by the reaction of propylene or isobutylene with molecular oxygen and ammonia at a temperature of between about 200 to 600° C. using the ammoxidation catalytic system of the invention.

Preferably, the process achieves a propylene conversion of at least 65%, more preferably at least 70% and most preferred at least 75% using the catalytic system of the invention.

Preferably, the selectivity in mol % to acrylonitrile is greater than 80%, more preferably greater than 85%. The yield of acrylonitrile in mol % is preferably greater than 50%, more preferably greater than 55%, even more preferably greater than 60% and most preferred greater than 65%.

EXAMPLES

The following examples are illustrative of some of the catalysts and methods of making and using the same falling within the scope of the present invention. They are, of course, not to be considered in any way limitative of the invention. Numerous changes and modifications can be made with respect to the invention.

The examples describe the preferred embodiments of the inventive method, which result in a final catalyst having improved performance. The catalysts prepared in the Examples have the empirical formula: $BiMoV_{0.095}Sb_{0.19}Nb_{0.21}O_x/50\%\ SiO_2$. The sequences of the preparation method are the same, while the conditions such as temperature and pH of the intermediate solutions are different.

All the tests of the resultant catalysts were performed under the same process operating conditions. Calcined catalysts were crushed to 35–60 mesh fraction. 5 g of each catalyst were charged into a tubular fixed bed stainless steel reactor. The reaction was carried out under 475° C. at atmospheric pressure with the following feed composition: propylene/$O_2$/$NH_3$/He=7.9/16.8/10/65.3 and a space velocity "W/F" of 3.

Example 1

The catalyst of this example was prepared according to the following procedure:

Part A: Formation of Vanadium Antimonate 10.2 g of $Sb_2O_3$ was slurried in 20ml water along with 3.18 g $V_2O_5$. The mixture was boiled until a paste was formed. The paste was then dried at 120° C. and calcined under airflow at 760° C. for 2 hrs.

Part B: Precipitation of Bismuth, Niobium and Molybdenum Mixed Oxide Hydrates

Solutions of 3.43 g niobium penta oxide hydrate 80% in 50 ml water, and 14.39 g $MoO_3$ in 36 ml water plus 15 ml concentrated $NH_4OH$ were prepared separately and then mixed together. The pH was adjusted to 3.8 using oxalic acid. Separately, 48.5 g $Bi(NO_3)_3 5H_2O$ was dissolved in 92 ml water plus 15 ml $HNO_3$ (concentrated). The bismuth solution was then added to the niobium/molybdenum solution and the pH was adjusted to 0.8 using $NH_4OH$. The mixture was stirred and boiled for ca. 1 hour and was then filtered and washed with 500 ml water.

Part C: Polycondensation of Silicic Acid

The pH of 111.5 g of silica colloidal 40 wt % was adjusted with diluted solution of $HNO_3$ to pH=1.9.

Final Catalyst Formulation 3.639 g of Part A, and the filter cake of Part B were added to Part C under vigorous stirring. The mixture was kept under vigorous stirring for 1 hour followed by boiling until paste formation. The paste was then dried at 120° C. and calcined under an airflow at 550° C.

Example 2

The catalyst of Example 2 was prepared according to same procedure followed in Example 1. However, while preparing Part C and after the addition of bismuth nitrate solution and ammonium hydroxide to the niobium/molybdenum solution, the resultant mixture was stirred for one hour without heating.

Example 3

The catalyst of Example 3 was prepared according to same procedure followed in Example 2, except that the pH of niobium/molybdenum solution was adjusted to 2.9.

Example 4

The catalyst of Example 4 was prepared according to same procedure followed in Example 3, except that Part A was prepared by boiling the slurry under refluxing until the mixture turns greenish-brown in color according to U.S. Pat. No. 4,405,498.

Example 5

The catalyst of Example 5 was prepared according to the same procedures followed in Example 3, except that bismuth nitrate penta hydrate was added directly to the niobium/molybdenum solution without prior dissolving.

Example 6

The catalyst of Example 6 was prepared according to same procedure followed in Example 3, except that 148.7 g of silica colloidial 30 wt % was used for Part C preparation, and the pH of niobium/molybdenum solution was equal to 4.0.

Example 7

The catalyst of Example 7 was prepared according to same procedure followed in Example 3, except that 148.7 g of silica colloidal 30 wt % was used for Part C preparation, and its pH was adjusted to 9.3.

TABLE I

Catalyst Activity Results

| Example No. | Propylene Conversion | Acrylonitrile Yield (%) | Acrylonitrile selectivity (%) |
|---|---|---|---|
| 1 | 85.0 | 72.5 | 85.4 |
| 2 | 96.4 | 77.0 | 79.8 |
| 3 | 85.6 | 72.3 | 84.5 |
| 4 | 80.8 | 68.8 | 85.2 |
| 5 | 86.3 | 68.8 | 79.7 |
| 6 | 95.0 | 77.7 | 81.8 |
| 7 | 94.9 | 78.1 | 82.3 |

As demonstrated by Examples 1 and 2, heating the precipitation product of bismuth, molybdenum and niobium is not advised at this stage of the preparation. It is believed that the heating decomposes/destroys polymeric molybdenum oxide hydrate species before being grown in an active crystalline form along with the other elements. Preferably, the resultant mixed hydrate oxides are produced without heat post-treatment.

The pH of the niobium/molybdenum solution is also shown to play an important role in the catalyst preparation. This is demonstrated by comparing the results of Examples 2 and 3, as well as the result of Examples 3 and 6. Increasing the pH from 2.6 (Example 3) to 3.8 (Example 2) or 4.0 (Example 6) results in a dramatic increase of catalyst activity expressed in product yield. Optimum pH is expected to be in the range of 3.5 to 10. However, it is noted in Example 7 that a further increase of the pH to 9.3 did not appreciably change the catalyst performance compared with a pH of 4.0 (Example 6).

Different procedures were described in the literature for formulating an active vanadium species (e.g., the vanadium antimonate) for ammoxidation reactions. One preferred embodiment employs the method set forth in the U.S. Pat. No. 4,405,498 which comprises the oxidation/reduction reaction between vanadium oxide ($V_2O_5$) and antimony oxide ($Sb_2O_3$), where a slurry of the oxides is boiled until the contained solids turn greenish-brown, indicating the interaction or partial reaction of the two metal oxides. This is followed by further drying and calcination between 550° C. and 750° C. Examples 3 and 4 demonstrate that only small induction of the reaction of both metal oxides is advised in the slurry reaction for a better catalyst performance.

According to one preferred embodiment of the invention, the mixed oxide hydrates of bismuth, molybdenum, and niobium are coprecipitated rapidly by rash or quick addition of bismuth nitrate solution to the niobium/molybdenum solution. The combining of a solution of bismuth and a niobium/molybdenum solution results in a more rapid precipitation. The rapid coprecipitation improves the resultant mixed oxide hydrates. This is a clearly demonstrated by comparing the results of Examples 3 and 5. In Example 5, bismuth nitrate penta hydrate was directly added to the niobium/molybdenum solution without prior dissolving and resulted in delayed/slow precipitation. In Example 3, $Bi(NO_3)_3 5H_2O$ was dissolved in 92 ml water with 15 ml $HNO_3$ and the bismuth solution was then added to the niobium/molybdenum solution. The yield achieved in Example 3 is greater than that achieved in Example 5.

The above description of the invention is intended to be illustrative and not limiting. Various changes or modifications in the embodiments described may occur to those skilled in the art. These can be made without departing from the spirit or scope of the invention.

What is claimed is:

1. A method for preparing a catalyst for olefin ammoxidation, comprising bismuth, molybdenum, vanadium, antimony, and niobium, comprising the steps of:
   (a) preparing a vanadium antimonate phase by heating a slurry of vanadium oxide and antimony oxide thereby forming a vanadium-antimony paste and subsequently drying the paste and calcining it to form said vanadium antimonate phase;
   (b) preparing a niobium-molybdenum solution by mixing niobium oxide hydrate and molybdenum oxide hydrate in water;
   (c) preparing bismuth, niobium, and molybdenum mixed oxide hydrates by adding bismuth to the niobium-molybdenum solution of step (b);
   (d) combining said vanadium antimonate phase, said bismuth, niobium and molybdenum mixed oxide hydrates and a support thereby forming a catalyst precursor mixture, wherein said mixed oxide hydrates are not subjected to heat treatment prior to forming said catalyst precursor mixture;
   (e) stirring the catalyst precursor mixture for a period of time sufficient to form a catalyst precursor paste; and
   (f) drying said catalyst precursor paste to form a dried catalyst precursor material and calcining said dried catalyst precursor material to form said catalyst.

2. The method of claim 1, wherein said vanadium oxide is $V_2O_5$.

3. The method of claim 2, wherein said antimony oxide is $Sb_2O_3$.

4. The method of claim 3, wherein said calcining in step (a) is at a temperature ranging from 700 to 850° C.

5. The method of claim 4, wherein said calcining in step (a) is at a temperature ranging from 740 to 780° C.

6. The method of claim 5, wherein said calcining in step (a) is at a temperature of about 750° C.

7. The method of claim 6, wherein said niobium-molybdenum solution has a pH of 3.5 to 5.

8. The method of claim 1, wherein said calcining in step (a) is at a temperature ranging from 600 to 950° C.

9. The method of claim 1, wherein said calcining in step (a) is in the presence of air.

10. The method of claim 1, wherein said niobium-molybdenum solution has a pH of 3.0 to 10.

11. The method of claim 1, wherein said niobium-molybdenum solution has a pH of 3.5 to 9.

12. The method of claim 1, wherein step (c) comprises precipitating said mixed oxide hydrates without heat treating said mixed oxide hydrates.

13. The method of claim 12, wherein step (c) comprises rapid co-precipitation of bismuth, niobium, and molybdenum mixed oxide hydrates.

14. The method of claim 1, wherein the bismuth addition of step (c) comprises adding a solution containing bismuth to said niobium-molybdenum solution.

15. The method of claim 1, wherein said support comprises pre-acidified silica.

16. The method of claim 1, wherein step (d) comprising incorporating said vanadium antimonate phase and said mixed oxide hydrates in pre-acidified silica colloidal.

17. The method of claim 1, further comprising boiling said catalyst precursor mixture to form said catalyst precursor paste.

18. The method of claim 17, wherein said stirring in step (e) is vigorous stirring.

19. The method of claim 18, wherein said catalyst precursor paste is dried at a temperature ranging from 100° C. to 150° C.

20. The method of claim 19, wherein said catalyst precursor paste is dried at a temperature ranging from 110° C. to 130° C.

21. The method of claim 20, wherein said catalyst precursor paste is dried at a temperature of about 120° C.

22. The method of claim 20, wherein said calcining of said dried catalyst precursor material is at a temperature ranging from 500 to 600° C.

23. The method of claim 22, wherein said calcining of said dried catalyst precursor material is at a temperature of about 550° C.

24. The method of claim 23, wherein said calcining of said dried catalyst precursor material is in the presence of air.

25. The method of claim 1, wherein said catalyst precursor paste is dried at a temperature ranging from 80° C. to 200° C.

26. The method of claim 1, wherein said calcining of said dried catalyst precursor material is at a temperature ranging from 450 to 650° C.

27. The method of claim 1, wherein said calcining of said dried catalyst precursor material is under an airflow.

28. The method of claim 1, wherein said support is selected from silica, alumina, zirconia, titania, alundum, silicon carbide, alumina-silica, inorganic phosphates, silicates, aluminates, borates and carbonates, pumice, montmorillonite, or mixtures thereof.

29. The method of claim 28, wherein said support is silica.

30. The method of claim 29, wherein said catalyst comprises 40–70% by weight support.

31. The method of claim 29, wherein said niobium-molybdenum solution is prepared using niobium derived from niobium pentoxide.

32. The method of claim 29, wherein said niobium-molybdenum solution is prepared using niobium derived from a niobium source soluble in water.

33. The method of claim 1, wherein said niobium oxide hydrate is derived from niobium pentoxide.

34. The method of claim 33, wherein step (a) comprises drying said paste at a temperature ranging from 80° C. to 200° C.

35. The method of claim 34, wherein step (a) comprises drying said paste at a temperature ranging from 100° C. to 150° C.

36. The method of claim 35, wherein step (a) comprises drying said paste at a temperature ranging from 110° C. to 130° C.

37. The method of claim 36, wherein step (a) comprises drying said paste at a temperature of about 120° C.

38. The method of claim 1, wherein said niobium oxide hydrate is derived from a niobium source which is soluble in water.

39. A method for preparing a catalyst for olefin ammoxidation, said catalyst containing bismuth, molybdenum, vanadium, antimony, and niobium, comprising the steps of:

(a) preparing a niobium-molybdenum solution at a pH of 3.5 to 10;

(b) adding bismuth to said niobium-molybdenum solution and precipitating bismuth, niobium, and molybdenum mixed oxide hydrates at room temperature and without heat post-treatment of said mixed oxide hydrates;

(c) combining a vanadium antimonate phase and said mixed oxide hydrates of bismuth, niobium, and molybdenum with pre-acidified silica colloidal thereby forming a catalyst precursor mixture;

(d) stirring the catalyst precursor mixture for a period of time sufficient to form a paste; and (e) drying said paste to form a dried material and calcining said dried material to form said catalyst.

40. A method for preparing a catalyst for olefin ammoxidation, said catalyst containing bismuth, molybdenum, vanadium, antimony, and niobium, comprising the steps of:

(a) preparing a vanadium antimonate phase;

(b) preparing a niobium-molybdenum solution at a pH of 3.5 to 5;

(c) adding bismuth to said niobium-molybdenum solution and precipitating bismuth, niobium, and molybdenum mixed oxide hydrates without heat post-treatment of said mixed oxide hydrates;

(d) combining said vanadium antimonate phase and said mixed oxide hydrates of bismuth, niobium, and molybdenum with pre-acidified silica colloidal thereby forming a catalyst precursor mixture;

(e) stirring the catalyst precursor mixture for a period of time sufficient to form a paste; and (f) drying said paste to form a dried material and calcining said dried material to form said catalyst.

* * * * *